US008775202B2

(12) United States Patent
Hanf et al.

(10) Patent No.: US 8,775,202 B2
(45) Date of Patent: *Jul. 8, 2014

(54) SYSTEM AND METHODS FOR DISTRIBUTED ANALYSIS OF PATIENT RECORDS

(75) Inventors: Thomas Hanf, Kansas City, MO (US); Christopher Finn, Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/651,102

(22) Filed: Dec. 31, 2009

(65) Prior Publication Data

US 2010/0106530 A1    Apr. 29, 2010

Related U.S. Application Data (62) Division of application No. 11/027,017, filed on Dec. 30, 2004.

(51) Int. Cl.

| G06Q 10/00 | (2012.01) |
|---|---|
| G06F 7/60 | (2006.01) |
| G06G 7/58 | (2006.01) |
| G06F 9/45 | (2006.01) |
| A61B 5/00 | (2006.01) |
| G06F 19/00 | (2011.01) |
| G06Q 50/24 | (2012.01) |
| G06Q 50/22 | (2012.01) |
| G06Q 10/10 | (2012.01) |

(52) U.S. Cl.
CPC ............... *G06Q 10/10* (2013.01); *G06Q 50/24* (2013.01); *G06Q 50/22* (2013.01)
USPC .................................................. 705/2; 705/3

(58) Field of Classification Search
USPC ........................................................ 705/2, 3, 4
See application file for complete search history.

(56) References Cited

U.S. PATENT DOCUMENTS

| 6,438,533 | B1 * | 8/2002 | Spackman et al. .............. 706/45 |
| 6,611,846 | B1 | 8/2003 | Stoodley |
| 2002/0087361 | A1 * | 7/2002 | Benigno et al. ................... 705/3 |
| 2002/0172335 | A1 * | 11/2002 | Narasimhan et al. ..... 379/106.02 |

(Continued)

OTHER PUBLICATIONS

Riva, et al., "The Personal Internetworked Notary and Guardian." International Journal of Medical Informatics 2000.

(Continued)

*Primary Examiner* — Sean K Hunter
(74) *Attorney, Agent, or Firm* — Shook Hardy & Bacon L.L.P.

(57) ABSTRACT

A system and associated methods provide healthcare entities with analyzing capabilities for records of a patient population. The analyzing process seeks to find matches between a piece of clinical knowledge introduced to a healthcare entity and data contained in the patient population records. According to one method, a service generates executable code based on the piece of clinical knowledge. Through a communication with the service, the healthcare entity makes a determination as to what extent the clinical knowledge has relevance to a patient population of the healthcare entity. Based on this determination, the healthcare entity receives at least a portion of the executable code. Then, the records of the patient population may be analyzed by the executable code to register matches of the clinical knowledge with data contained within the records. System activity may then be initiated based on the matches registered.

10 Claims, 5 Drawing Sheets

(56) References Cited

U.S. PATENT DOCUMENTS

| | | | |
|---|---|---|---|
| 2002/0184325 A1* | 12/2002 | Killcommons et al. | 709/206 |
| 2003/0074225 A1 | 4/2003 | Borsand et al. | |
| 2003/0078813 A1* | 4/2003 | Haskell et al. | 705/3 |

OTHER PUBLICATIONS

Non-Final Office Action mailed Feb. 3, 2010 in U.S. Appl. No. 11/027,017.

Non-Final Office Action Mailed Sep. 1, 2010 in U.S. Appl. No. 12/651,105.

Final Office Action Mailed Oct. 21, 2010 in U.S. Appl. No. 11/027,017.

Non-Final Office Action Mailed Apr. 18, 2011 in U.S. Appl. No. 11/027,017.

Final Office Action Mailed May 10, 2011 in U.S. Appl. No. 12/651,105.

Non-Final Office Action mailed Sep. 21, 2011 in U.S. Appl. No. 12/651,105.

Final Office Action mailed Oct. 13, 2011 in U.S. Appl. No. 11/027,017.

Final Office Action mailed Apr. 27, 2012, in U.S. Appl. No. 12/651,105, 14 pages.

Non-Final Office Action mailed Dec. 18, 2012 in U.S. Appl. No. 11/027,017, 13 pages.

Non-Final Office Action mailed May 8, 2013 in U.S. Appl. No. 12/651,105; 12 pages.

Final Office Action mailed Mar. 26, 2013 in U.S. Appl. No. 11/027,017, 17 pages.

Final Office Action mailed Sep. 16, 2013 in U.S. Appl. No. 12/651,105; 25 pages.

Non-Final Office Action mailed Oct. 4, 2013 in U.S. Appl. No. 11/027,017, 16 pages.

* cited by examiner

SYSTEM AND METHODS FOR DISTRIBUTED ANALYSIS OF PATIENT RECORDS

CROSS-REFERENCE TO RELATED APPLICATIONS

This application is a divisional of U.S. patent application Ser. No. 11/027,017 filed Dec. 30, 2004, entitled "System and Method for Distributed Analysis of Patient Records" and is related by subject matter to U.S. patent application Ser. No. 12/651,105 entitled "System and Method for Distributed Analysis of Patient Records" filed on the same date, both of which are assigned or under obligation of assignment to the same entity as this application and incorporated in this application by reference.

BACKGROUND OF THE INVENTION

The present invention relates generally to the field of computer software. More particularly, the present invention relates to a computerized system and methods for distributed analysis of records of a patient population in view of certain clinical knowledge.

Standardized medical or healthcare knowledge ("clinical knowledge") has traditionally been introduced to clinicians in a number of different ways. For instance, a clinician may participate in health-related degree programs at colleges or universities, or attend healthcare seminars, to gain clinical knowledge. Clinicians may also review a wide variety of information sources for clinician knowledge, such as professional journals, reference books and guides, and government agency notices. Uniform and widespread dissemination of portions of clinical knowledge over a large number of clinicians, however, can be quite difficult. For one thing, clinicians do not all consult the same sources for clinical knowledge. Moreover, time and resource constraints often force many practicing clinicians to simply conduct a cursory review of the sources relevant to their practice. Therefore, as new standards of care and related knowledge are accepted in the healthcare community, there is a problem with integrating this information into the practice habits of clinicians so that patients receive the highest level of care.

One method of improving the dissemination and review of healthcare-related information representing clinical knowledge is for clinicians to automatically receive such information through electronic updates. These updates may be delivered by enrolling with, for example, a listserv or other automated emailing list, enabling a large number of clinicians to receive the healthcare-related information with minimal effort. Even with the convenience and ease of these types of information distribution methods, however, a given clinician may not be capable of reviewing and retaining all of the clinical knowledge received over a given period of time. Furthermore, such a clinician may not have a manageable and efficient way to relate the information to a plan of care for each patient for whom the clinician provides healthcare services. To illustrate, suppose that a clinician employs an assistant or other clinician to review sources of new healthcare knowledge and pull all patient records to determine if the information has relevance to any particular patient's plan of care. Such a scheme would, unfortunately, be very time consuming, and open to human error due to the subjective interpretations of the assistant. In some instances, it may be impossible to discover and contact all of the patients that may be at risk in view of the clinical knowledge. One example would be when clinical knowledge includes an alert about a specific chronic health crisis such as new knowledge that a particular medication is inappropriate when administered to a certain patient population. In other instances, this method would slow the dissemination of clinical knowledge regarding new treatments.

A solution is needed for automating the review of patient records for a given healthcare entity to identify instances where certain acquired clinical knowledge has relevance to providing patient care.

BRIEF SUMMARY OF THE INVENTION

A system and associated methods of the present invention analyze records of a patient population based on the receipt of a piece of clinical knowledge. In one aspect of the invention, a method in a computer system of queuing tasks is provided. These tasks affect a portion of a patient population of a healthcare entity. According to the method, executable code is generated and distributed to the healthcare entity, the code being based on the piece of clinical knowledge. Taking into account certain rules of the healthcare entity, the method then involves the steps of selectively accessing a set of records of the patient population and analyzing such records by the executable code to register matches of the piece of clinical knowledge with data contained in the set of records. With the results of the matching process, a task list may be generated that affects a select group of the set of records where matching occurred.

Another aspect of the present invention includes a method in a computer system for presenting a healthcare entity with an option to automatically analyze a set of records of the healthcare entity's patient population, wherein the analysis relates to a piece of clinical knowledge. According to the method, a publication associated with the piece of clinical knowledge is received and executable code is generated based on the publication. This executable code is configured to perform an analysis within the set of records. A link to the executable code may then be distributed and presented to the healthcare entity. Acceptance of the link causes the executable code to be distributed and the set of patient records to be analyzed to thereby register matches of the piece of clinical knowledge with data contained in the set of records.

Provided in another aspect of the present invention is a method in a computer system for automatically implementing an analysis of a set of records of the patient population of the healthcare entity, wherein the analysis relates to a piece of clinical knowledge. According to the method, a healthcare entity first receives executable code incorporating the piece of clinical knowledge. The code is configured to perform an analysis within the set of records. The set of records may then be accessed and analyzed by running the executable code. Analyzing of the records includes registering matches of the piece of clinical knowledge with data contained in the set of records.

In yet another aspect of the present invention, a method is provided for analyzing a set of records of a patient population of a healthcare entity with respect to a piece of clinical knowledge. According to the method, executable code is first generated based on the piece of clinical knowledge. The healthcare entity then determines the extent to which the clinical knowledge has relevance to the patient population, and based on this relevance determination, distributes at least a portion of the executable code to the healthcare entity. The set of records may then be accessed and analyzed by running the executable code. Analyzing the records includes registering matches of the piece of clinical knowledge with data contained in the set of records. Subsequently, system activity may be initiated based on the particular matches generated.

BRIEF DESCRIPTION OF THE SEVERAL VIEWS OF THE DRAWING

In the accompanying drawings which form a part of the specification and are to be read in conjunction therewith and in which like reference numerals are used to indicate like elements in the various views.

DETAILED DESCRIPTION OF THE INVENTION

The invention provides a system and associated methods enabling electronic analysis of records of a patient population of a healthcare entity for certain conditions related to a standardized piece of clinical knowledge. Through the use of the present system and methods, a more automated process for knowledge dissemination and condition checking may be realized. This ensures that patients have a greater chance of receiving from their clinician the generally accepted standard of care in the medical or healthcare community.

General Computing System Environment

Figure 1:
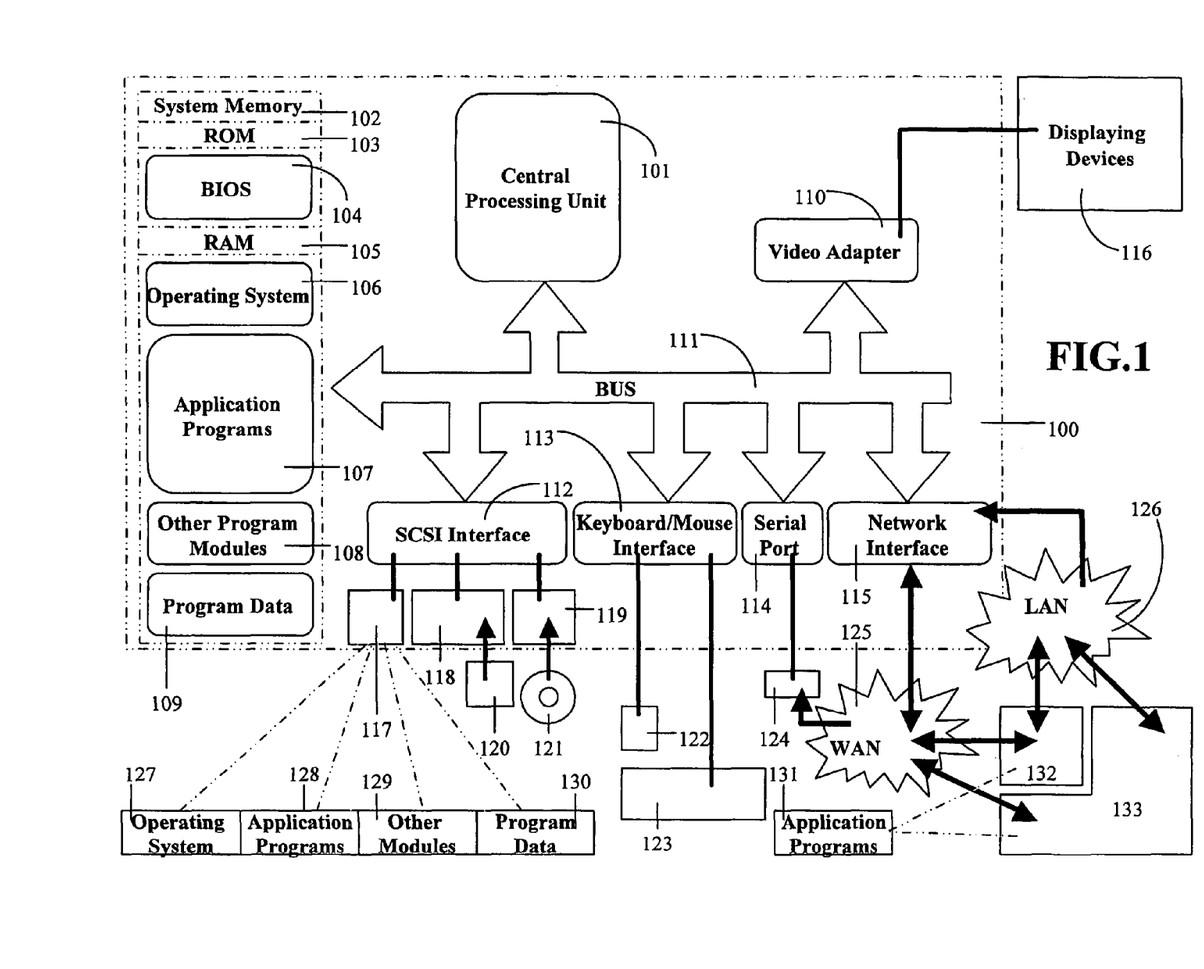
FIG. 1 is a block diagram of an exemplary computing system suitable for use in implementing the present invention.

FIG. 1 illustrates an example of a suitable computing system environment in which the invention may be implemented. The computing system environment is only one example of a suitable computing environment and is not intended to suggest any limitation as to the scope of use or functionality of the invention. Neither should the computing system environment be interpreted as having any dependency or requirement to any one or combination of components illustrated in the exemplary operating environment.

The present invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, cellular telephones, portable wireless devices, multiprocessor systems, microprocessor-based systems, programmable consumer electronics, network PCs, minicomputers, mainframe computers, distributed computing environments that include any of the above systems or devices, and the like.

The present invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the invention includes a general purpose computing device in the form of a computer system 100. System 100 serves at least in part as a general medical information system. Components of system 100 include, but are not limited to, a processing unit 101, a system memory 102, and a system bus 111 that couples various system components including the system memory 102 to the processing unit 101. The system bus 111 may be any of several types of bus structures including a memory bus or memory controller, a peripheral bus and a local bus using any of a variety of bus architecture. By way of example, and not limitation, such architectures include Industry Standard Architecture (ISA) bus, Micro Channel Architecture (MCA) bus, Enhanced ISA (EISA) bus, Video Electronics Standard Association (VESA) local bus, and Peripheral Component Interconnect (PCI) bus also known as Mezzanine bus.

System 100 typically includes a variety of computer readable media. Computer readable media can be any available media that can be accessed by system 100 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is mot limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by system 100. Communications media typically embodies computer readable instructions, data structures, program modules or other data in a modulated data signal such as a carrier wave or other transport mechanism and includes any information delivery media. The term "modulated data signal" means a signal that has on or more of its characteristics set or changed in such a manner as to encode information in the signal. By way of example, and not limitation, communication media includes wired media such as a wired network or direct wired connection, and wireless media such as acoustic, radio frequency (RF), infrared and other wireless media. Combinations of any of the above should also be included within the scope of computer readable media.

The system memory 102 includes computer storage media in the form of a volatile and/or nonvolatile memory such as read only memory (ROM) 103 and random access memory (RAM) 105. A basic input/output system (BIOS) 104, containing the basic routines that help to transfer information between elements within system 100, such as during start-up, is typically stored in ROM 103. RAM 105 typically contains data and/or program modules that are immediately accessible to and/or presently being operated on by processing unit 101. By way of example, and not limitation, FIG. 1 illustrates operating system 106, application programs 107, other program modules 108, and program data 109.

The system 100 may also include other removable/nonremovable, volatile/nonvolatile computer storage media. By way of example only, FIG. 1 illustrates a hard disk drive 117 that reads from or writes to nonremovable, nonvolatile magnetic media, a magnetic disk drive 118 that reads from or writes to removable, nonvolatile magnetic disk 120, and an optical disk drive 119 that reads from or writes to a removable, nonvolatile optical disk 121 such as a CD-ROM, DVD-ROM or other optical media. Other removable/nonremovable, volatile/nonvolatile computer storage media that can be used in the exemplary operating environment include, but are not limited to, magnetic tape cassettes, flash memory cards, digital video disks, digital video tape, Bernoulli cartridges, solid state RAM, solid state ROM, and the like. The hard disk drive 117, magnetic disk drive 118 and optical disk drive 119 are typically connected to the system bus 111 by a Small Computer System Interface (SCSI) 112. Alternatively, the hard disk drive 117, magnetic disk drive 118 and optical disk drive 119 may be connected to the system bus 111 by a hard disk drive interface, a magnetic disk drive interface, and an optical drive interface, respectively.

The drives and their associated computer storage media discussed above and illustrated in FIG. 1, provide storage of computer readable instructions, data structures, program modules and other data for the system 100. In FIG. 1, for example, hard disk drive 117 is illustrated as storing operating system 127, application programs 128, other program modules 129, and program data 130. Note that these components can either be the same as or different from operating system 106, application programs 107, other program modules 108, and program data 109. A user may enter commands and information into the system 100 through input devices such as a keyboard 123 and pointing device 122, commonly referred to as a mouse, trackball or touch pad. Other input devices (not shown) may include a microphone, joystick, game pad, satellite dish, scanner, or the like. These and other input devices are often connected to the processing unit 101 through a user input interface 113 or a serial port interface 114 that is coupled to the system bus 111, but may be connected by other interface and bus structures, such as a parallel port, game port or a universal serial bus (USB). A monitor 116 or other type of display device is also connected to the system bus 111 via an interface, such as a video adapter 110. In addition to the monitor 116, computers may also include other peripheral output devices such as speakers and printers, which may be connected through an output peripheral interface.

The system 100 may operate in a networked environment using logical connections to one or more remote computers, such as a remote computer 133 and/or other electronic devices, such as a communication device 132. The remote computer 133 may be a personal computer, a server, a router, a network PC, a peer device or other common network node, and typically includes many or all of the elements described above relative to the system 100, although only a memory storage device has been illustrated in FIG. 1. Remote computer 133 may, for example, be found at a variety of health system related locations, such as hospitals, other inpatient settings, pharmacies, a clinician's office/practice, ambulatory settings, testing labs and a patient's home environment, though other locations may be chosen as well. The communication device 132 may be a mobile cellular phone, mobile text-pager or other portable communications device, and typically includes some of the elements described above relative to the system 100. The logical connections depicted in FIG. 1 include a local area network (LAN) 126 and a wide area network (WAN) 125, but may also include other networks. Such networking environments are commonplace in offices, enterprise-wide computer networks, intranets and the Internet.

When used in a LAN networking environment, the system 100 may be connected to the LAN 126 through a networking interface or adapter 115. When used in a WAN networking environment, the system 100 typically includes a modem 124 or other means for establishing communications over the WAN 125, such as the Internet. The modem 124, which may be internal or external, may be connected to the system bus 111 via the serial port interface 114 or other appropriate mechanism. In a networked environment, program modules depicted relative to the system 100, or portions thereof, may be stored in the remote storage device. By way of example, and not limitation, FIG. 1 illustrates remote application programs 131 as residing on memory devices 132 and 133. It will be appreciated that the network connections shown are exemplary and other means of establishing a communications link between the computers and/or portable communication devices may be used.

Although many other internal components of the system 100 are not shown, those of ordinary skill in the art will appreciate that such components and the interconnection are well known. Accordingly, additional details concerning the internal construction of the system 100 need not be disclosed in connection with the present invention.

Those skilled in the art will understand that program modules such as the operating system 106 and 127, application programs 107 and 128, and program data 109 and 130 are provided to the system 100 via one of its memory storage devices, which may include ROM 103, RAM 105, hard disk drive 117, magnetic disk drive 118 or optical disk drive 119. Preferably, the hard disk drive 117 is used to store program data 130 and 109, application programs 107 and 128, and operating system 106 and 127.

When the system 100 is turned on or reset, the BIOS 104, which is stored in the ROM 103 instructs the processing unit 101 to load the operating system from the hard disk drive 117 into the RAM 105. Once the operating system 127 is loaded in RAM 105, the processing unit 101 executes the operating system code and causes the visual elements associated with the user interface of the operating system 127 to be displayed on the monitor 116 or other display device. When an application program 107 and 128 is opened by a user, the program code and relevant data are read from the hard disk drive 117 and stored in RAM 105.

Patient Record Analysis

Figure 2:
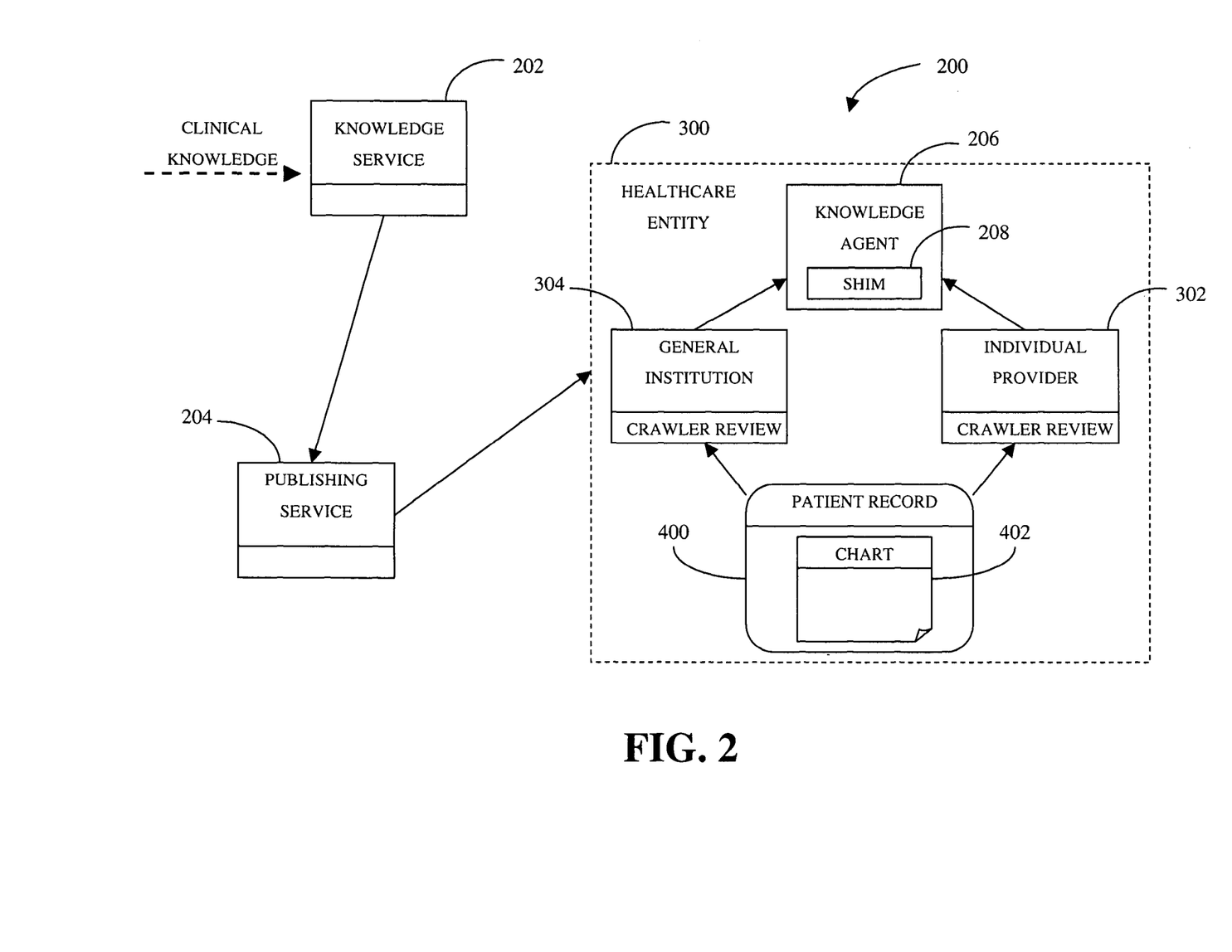
FIG. 2 is a block diagram of one embodiment of a set of component modules of the present invention illustrating the functional relationship of the modules with a healthcare entity.

Illustrated in FIG. 2 is the general flow of activity through a set of general component modules 200 (functioning within the system 100) and interfacing with certain elements of a healthcare entity 300. The general component modules 200 accomplish analysis of patient records of the healthcare entity 300 for certain conditions related to clinical knowledge that is being introduced to the entity 300.

Various terminology discussed with respect to the present invention may have particular meaning as described below. For instance, the term "clinician" includes, but is not limited to, a treating physician, specialists such as surgeons, radiologists and cardiologists, emergency medical technicians, physician's assistants, nurse practitioners, nurses, physical therapists, pharmacists, dieticians, microbiologists, and the like, and aides or assistants thereto. The term "patient" refers to a person that is receiving or has received health-care-related services in any location in a medical environment (e.g., hospitals or other inpatient or outpatient settings, a clinician's office/practice location, ambulatory settings, testing labs, patient's home environment, or in any other setting). The component modules, as well as elements of the healthcare entity 300, may interact with various types of informational databases containing certain types of general medical information, as well as interacting with medical records that contain information about specific patients. As an example, these medical records may take the form of an electronic medical record (EMR) for a particular patient. The electronic medical record is typically designed to contain various types of data about an individual patient, such as: patient identifying information; insurance and financial information; patient health status, such as observed conditions of the patient (e.g., physiological conditions such as blood pressure, oxygen saturation levels in blood, or other "vital signs"), medications taken and current immunizations, food and drug allergies, diagnoses of various clinicians; and care documentation including a listing of clinicians that are currently providing or that have provided care to the patient. Any or all of the information in the electronic medical record may be organized into one or more structured charts (or documents) within the record. In one embodiment, the EMR may take the form of a continuity of care record (CCR) in which the data are stored in a structured manner. It should be understood, however, that the term "medical record", "patient record" or "electronic medical record" in particular, should not be interpreted to be limited to any type of computer-readable format or record, but includes any electronically-stored data structure containing information relative to at least one specific patient and from which information may be viewed and/or extracted by the system of the present invention. The term "healthcare entity" is meant to denote any organization or institution forming an overall healthcare delivery system or network, or any subcomponents thereof functioning individually or collectively with other subcomponents (e.g., health system related locations such as hospitals or medical offices, individual providers such as clinician or group practices, among others).

Turning now to a more detailed description of the general component modules 200, as seen in FIG. 2, component modules 200 include a Knowledge Service 202, a Publishing Service 204 and a Knowledge Agent 206. Clinical knowledge generated or otherwise acquired by the Knowledge Service 202 is published electronically or in hardcopy as an informational publication for transmission to the Publishing Service 204. In turn, the Publishing Service 204 extracts necessary information from the content of the publication to generate executable computer code or instructions based a specific piece of clinical knowledge of the publication. The executable code may be distributed by transmission or "download" to the healthcare entity 300 (e.g., through Knowledge Agent 206) for automated analysis of patient records of the entity 300. More specifically, the executable code preferably includes a structured query adapted to "crawl" or search through electronic patient records 400 residing with (or networked with) the entity 300 to find occurrences of matching conditions between the clinical knowledge and data or information stored within the patient records, and "flag" or record such matches. In an embodiment, the information is stored in a structured manner so that matching conditions are generally satisfied by exact matching. In other embodiments, fuzzy matching may be employed. Based on the results of the search (i.e., the particular matches flagged), various system activity within or through healthcare entity 300 may be initiated, as explained in further detail below.

In an embodiment, the system activity is creating a task list for human (i.e., the clinician) use or further automated processing. A brief list of other exemplary system activities that may be directly initiated or included on the task list include: generating reports about the matching results; automated contacting of patients and/or healthcare providers relevant to the matches; or editing of standard of care guidelines (or protocols) for clinicians that are located within files of the healthcare entity 300. The activities may be queued or initiated for all clinical records that are matched. Alternatively, for activities having less immediate clinical impact, each activity may be tied to a specific event, such as the next time a chart is opened or the next renewal of a medication. Additionally, combinations of the system activities may be implemented. For instance, the clinical knowledge may relate to a change in drug formulary for a specific insurance company that provides health insurance coverage for certain patients of the healthcare entity 300. In other words, the "preferred drug" that the insurance company had been fully covering for treatment of a given condition may change to a different brand or type of drug (e.g., a generic of the previous preferred drug). Once a search for matches of the health insurance coverage with associated patients is complete, multiple system activities may be launched including (a) creating an event to queue renewal events for a group of patients, and (b) notifying clinicians that treat such patients by email of the formulary change. For example, a renewal event may set an alert to suggest a generic alternative when a patient from the patient group requests a renewal. It should be understood that the aforementioned system activities are not meant to form an exhaustive list of activities that are contemplated by the present invention. Additionally, the system activity may be carried out through an individual provider 302 and/or a general institution 304 forming at least a part of the healthcare entity 300. Such system activity may be relevant to flagged matches for specific records of patients that receive care directly from the respective provider 302 or institution 304. The executable code including the structured query may be referred to hereinafter as the "crawler".

The Knowledge Service 202 is preferably an organization recognized as an authority for medical or healthcare-related clinical knowledge. For instance, the Knowledge Service 202 may be a federal agency such as the Centers for Disease Control (CDC), the Food and Drug Administration (FDA), or other agency, or may be a medical/healthcare group or educational institution, content publishing company, or other industry member (e.g., pharmaceutical company) recognized by the healthcare entity as an authority on matters regarding particular clinical knowledge. As more fully explained below, the specific clinical knowledge may relate to a wide range of information. For instance, the specific clinical knowledge may include, but is not limited to, generally accepted standards of care (e.g., treatment guidelines for specific health conditions or clinical circumstances, changes in evidence-based medicine standards, etc.), adverse or other atypical drug reactions (ADRs) and the like (e.g., drug-drug interactions, recognized drug or food allergies, among others), and alerts about specific public health situations (e.g., illness epidemics or pandemics, bio-terrorism attacks, drug recalls, among others).

It should be understood that the Publishing Service 204 may be co-located with or otherwise controlled by the Knowledge Service 202, such that the Knowledge Service 202 manages activities of the Publishing Service 204, including the generation of the crawler by the Publishing Service 204 and distributing of the crawler to the Knowledge Agent 206. On the other hand, Publishing Service 204 may be independent of the Knowledge Service 202, and receive only minimal or no guidance from the Knowledge Service 202 in how the clinical knowledge should be used to enable analyzing of the electronic patient records 400 of the healthcare entity 300.

In embodiments where the Knowledge Service 202 provides the informational publication in electronic form, the Publishing Service 204 may utilize a computer program to automatically extract the specific information embodied in the clinical knowledge. Such clinical knowledge information may then be used to generate executable code for analyzing the patient records to register associated matches. Alternatively, if the informational publication is not provided by the Knowledge Service 202 in electronic form, or if automatic extraction is not desired, then the Publishing Service 204 may employ persons as clinical knowledge reviewers to review the publication produced by the Knowledge Service 202 and generate the crawler based on the clinical knowledge.

One form of the crawler may be as a macro configured to operate with one or more computer platforms and operating systems of the healthcare entity 300 to reach and extract information organized within the electronic patient record 400 residing with the entity 300. More specifically, the structured queries of the macro extract the information from various fields of a structured chart 402 residing with each electronic patient record 400, as will be more fully explained below with reference to FIG. 3. Regardless of the form of the crawler, the underlying executable code is preferably digitally signed code, authenticating that the source of origin for the code is the recognized Publishing Service 204 (i.e., a trusted source). The structured queries embodied in the executable code may also take a structured query language (SQL) format. Alternatively, other formats such as XML-oriented and RDF-oriented querying may be employed. Furthermore, more than one crawler may be generated by the Publishing Service 204 for each piece of clinical knowledge so that different crawlers may be authorized to engage in different healthcare entity 300 system activities. For instance, one crawler may be responsible for queuing tasks for clinicians based on matches uncovered during analysis, and another crawler may have the responsibility of generating a report based on the analytical results. Each crawler preferably has within the authenticating signed code a manifest that informs the healthcare entity 300 about the activities the specific crawler is authorized to perform.

By way of two examples, the executable code may take the form of a portable XML structure. For purposes of the examples, a portion of a Continuity of Care Record (CCR) containing standard elements (demographic information, payer information, allergies, medications, etc.) is provided. In this example, the record is represented in human readable format rather than codified according to a standard medical nomenclature.

```
<CCR>
    <Demographics>
        <PatientFirstName>John</PatientFirstName>
        <PatientLastName>Doe</PatientLastName>
        <DOB>12/23/1999</DOB>
        <Phone>913-555-1010</Phone>
        <MRN>123-45-6789</MRN>
    </Demographics>
    <Eligibility>
        <Payer>Quacking Duck Insurance</Payer>
        <Plan>12345</Plan>
        <Group>98765</Group>
    </Eligibility>
    <Allergies>
        <Allergy>latex</Allergy>
    </Allergies>
    <CurrentMedications>
        <Medication>
            <Substance>simvastatin</Substance>
            <Brand>Zocor</Brand>
            <Dose>10mg</Dose>
            <RxExpires>03/31/2005</RxExpires>
```

-continued

```
        </Medication>
    </CurrentMedications>
</CCR>
```

In a first example, a crawler is generated to inform members of a payer plan and the relevant physicians that a first medication offered under the trademark ZOCOR is no longer a formulary and suggest that a second medication offered under the trademark LIPITOR be offered at the next renewal. The clinical knowledge required for a match is the membership in the plan ("XYZ Insurance") and a current medication of ZOCOR. In this example, the macro may be represented as an XQuery that produces an XML structure suitable for importation and execution within other systems:

```
<TaskList>
{
    for $pat in doc("ccr.xml")/CCR/Demographics,
        $elig in doc("ccr.xml")/CCR/Eligibility,
        $med := doc("ccr.xml")/CCR/CurrentMedications
    where $elig/Payer="XYZ Insurance" and
        $elig/Plan=12345 and
        $elig/Group=98765 and
        $med/Medication/Brand="Zocor"
    return
        <Task type="Substitution Notification">
            <ContactName>
            $pat/FirstName $pat/LastName
            </ContactName>
            <ContactMRN>
            $pat/MRN
            </ContactMRN>
            <TaskActiveDate>
            $med/Medication/RxExpires
            </TaskActiveDate>
            <SubstituteMedication>Lipitor
            </SubstituteMedication>
        </Task>
}
<TaskDetails>
Zocor has moved to an off-formulary status. Quacking Duck Insurance
recommends a substitution of Lipitor, which is now on formulary.
</TaskDetails>
</TaskList>
```

An executable suitable for delivery or association with the CCR would result as follows if a match is found during the analysis of the CCR:

```
<TaskList>
<Task type="Substitution Notification">
    <ContactName>John Doe</ContactName>
    <TaskActiveDate>03/31/2005</TaskActiveDate>
    <SubstituteMedication>Lipitor</SubstituteMedication>
</Task>
<TaskDetails>
Zocor has moved to an off-formulary status for your group. XYZ
Insurance recommends a substitution of Lipitor, which is now
on formulary.
</TaskDetails>
</TaskList>
```

In a second example using the same CCR, assume a content provider responsible for monitoring FDA bulletins determines that the medication sold under the trademark ZOCOR is known to produce a higher incidence of toxic shock in patients with latex allergies. In this example, the macro may be represented as an XQuery that produces an XML structure as follows:

```
<TaskList>
{
    for $pat in doc("ccr.xml")/CCR/Demographics,
        $allergies in doc("ccr.xml")/CCR/Allergies,
        $med := doc("ccr.xml")/CCR/CurrentMedications
    where $allergies/Allergy="latex"
        $med/Medication/Brand="Zocor"
    return
        <Task type="Discontinue Notification">
            <ContactName>
            $pat/FirstName $pat/LastName
            </ContactName>
            <ContactMRN>
            $pat/MRN
            </ContactMRN>
            <ContactPhone>
            $pat/Phone
            </ContactPhone>
            <TaskAction>Call to discontinue</TaskAction>
        </Task>
}
<TaskDetails>
Zocor has been found to increase risk of toxic shock in patients
having an allergy to latex. The FDA recommends discontinuing
use of Zocor and substitution of an alternative statin in such
patients.
</TaskDetails>
</TaskList>
```

An executable for the task list (and suitable for other applications) would result if a match is found during the analysis of the CCR:

```
<TaskList>
<Task type="Discontinue Notification">
    <ContactName>John Doe</ContactName>
    <ContactPhone>913-555-1010</ContactPhone>
    <ContactMRN>123-45-6789</ContactMRN>
    <TaskAction>Call to discontinue</TaskAction>
</Task>
<TaskDetails>
Zocor has been found to increase risk of toxic shock in patients having
an allergy to latex. The FDA recommends discontinuing use of Zocor
and substitution of an alternative statin in such patients.
</TaskDetails>
</TaskList>
```

Distributing and implementing of the crawlers may be regulated by certain policies of the healthcare entity 300. As an example, if the activities to be queued or initiated relate to new standards of care for pediatric patients with a certain disease or other illness who take a given medication, and the healthcare entity 300 does not treat pediatric patients, then analyzing the entity's patient records for such matching health status/course of treatment information would be unnecessary, and will not be implemented.

One way to enable such regulation is to have the healthcare entity 300 review the distributed crawler to first determine if the underlying clinical knowledge referenced in the executable code is relevant to the patients of the entity 300. If there is no relevance, then analyzing of the patient records will not take place. One the other hand, if there is relevance, then the executable code will pass to the Knowledge Agent 206 to perform the analyzing of the electronic patient records 400. Such a review could be done electronically in accordance with certain procedures established by the healthcare entity 300. According to an alternative method, the healthcare entity 300 may instead first receive an electronic link or reference instruction related to the executable code, such as a uniform resource identifier (URI). This allows authorized individuals of the healthcare entity 300 to decide whether to distribute and implement the portion of executable code that includes the structured query by either selecting or not selecting the electronic link. If the link is selected, then distributing of the executable code to the Knowledge Agent 206 may commence. In either case, delivery of the executable code and/or electronic links thereto by the Publishing Service 204 to the healthcare entity 300 may be on a subscription basis. The subscription may be engaged via a synchronous polling mechanism or asynchronously by email or other messaging system (e.g., by text messaging). For example, the synchronous polling mechanism includes, in one embodiment, an RSS formatted feed of summary information detailing what clinical knowledge each crawler contains, and the URIs necessary to access the given crawler. In other embodiments, crawlers may be distributed on an ad hoc basis or at predetermined scheduled times.

The Knowledge Agent 206 may take the form of a virtual machine providing the interface for the respective provider 302 or institution 304 to employ the crawler to analyze the patient records of the given provider 302 or institution 304. In one embodiment, the virtual machine is a Java virtual machine running Java byte code, enabling the Knowledge Agent 206 to run on any number of operating systems, such as Windows, Unix, or others. Various shims 208, or program elements, may be integrated with the virtual machine to provide the end user of the healthcare entity 300 with control over the action of Knowledge Agent 206. For instance, shims 208 facilitate the representation of the results of the analysis by the crawler to the end user (e.g., list of patients that are at risk due to a new ADR guideline, etc.), and may control, based on analysis results, automated system actions pre-established by the healthcare entity 300. In the embodiment described above in which portable XML structures are imported through an interface into the local EMR system, a shim may provide exposure of the electronic medical record in an XML format. Alternatively, a shim may execute the macro directly in the environment. In either example, the output of the macro may be a task list including one or more XML descriptors. The descriptors are capable of initiating other activities when consumed by other applications responsible for the activities.

As referenced above, electronic patient medical records 400 may optionally take the form of standardized continuity of care records, or derivatives thereof, containing the structured charts 402 where specific patient information resides. One particular format for these structured charts 402 that may be implemented is the clinical document architecture format (CDAF). It should be understood that other formats may provide the necessary framework and information field organization for the structured charts to enable analyzing of the patient records by the executable code that is based on the clinical knowledge. In addition to standard patient and delivery of care information, structured charts 402 may contain chart formatting information accessible by the executable code and the system administrators for a network operating with the healthcare entity 300. This chart formatting information includes, as examples, version identifiers (e.g. XML 1.7), vendor identifiers and standard identifiers for the given chart 402.

Figure 3:
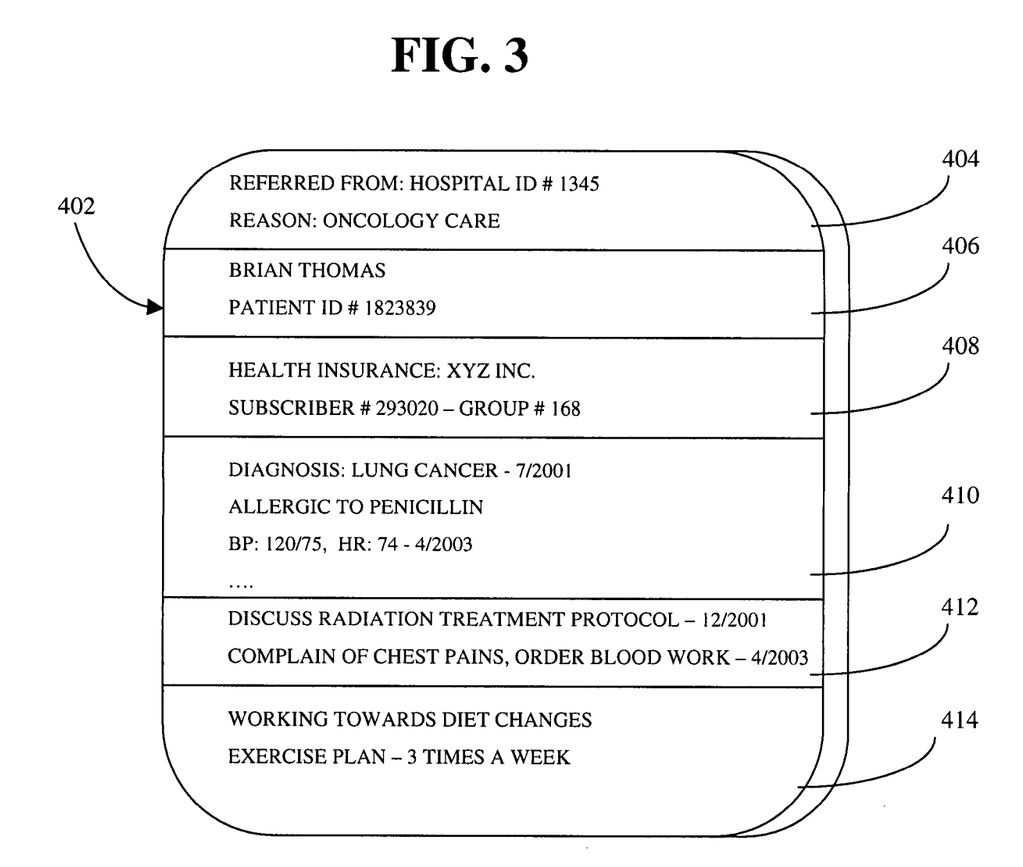
FIG. 3 is an exemplary structured chart for analyzing in accordance with the present invention.

With reference to FIG. 3, one exemplary structured chart 402 that may be analyzed by the structured query embodied in the executable code is depicted. The chart 402 contains a number of field categories for the patient from which information may be extracted, including: document identifying information 404, such as where the patient was referred from and reasons for the referral; patient identifying and contact information 406; insurance and financial information for the patient 408; health status information 410 for the patient, such as diagnoses and problems, social history and risk factors (e.g., smoker), adverse reactions and allergies, current medications and immunizations, measured vital signs, laboratory results (e.g., blood sugar, hemoglobin in a blood sample), and procedures the patient has undergone; care documentation 412 including clinicians' documentation of previous encounters with the patient; and care plan recommendations 414 for the patient.

As a matter of illustration of structured chart 402 content examination, suppose that new clinical knowledge has been established relating to increased risk of heart attack and stroke incidence when a person having certain risk factors is undergoing hormone replacement therapy (HRT). A crawler may be created by the Publishing Service 204 related to this clinical knowledge and distributed to the healthcare entity 300 (e.g., either automatically or after approving of the crawler by selecting a link to distribute the crawler). The crawler, through for example the Knowledge Agent 206, may then be executed to find one or more matching patient records where information in the respective structured chart 402 fields indicate that such patients receive HRT and have one or more of the particular risk factors. For example, the risk factors for these patients corresponding with the matching patient records may include their gender (e.g., female), certain social history and risk factor information (e.g., a smoker, exceedingly high body mass index number and/or weight, etc.), or other factors. For each match flagged, certain system activities may then commence, such as queuing a list of matching patients including contact information to set up appointments to meet with a clinician about their health status and plan of care. The queued list is preferably ranked according to the severity of the risk factors and/or the total number of risk factors for each matching patient. The clinical knowledge represented by the crawler, along with information gathered from other sources available to Knowledge Agent 206 (e.g., from electronically searchable clinical knowledge databases such as Multum, SNOMED-CT, ICD-9, and others), provides an information set allowing the crawler to execute the ranking, or other evaluation of the matching results.

Figure 4:
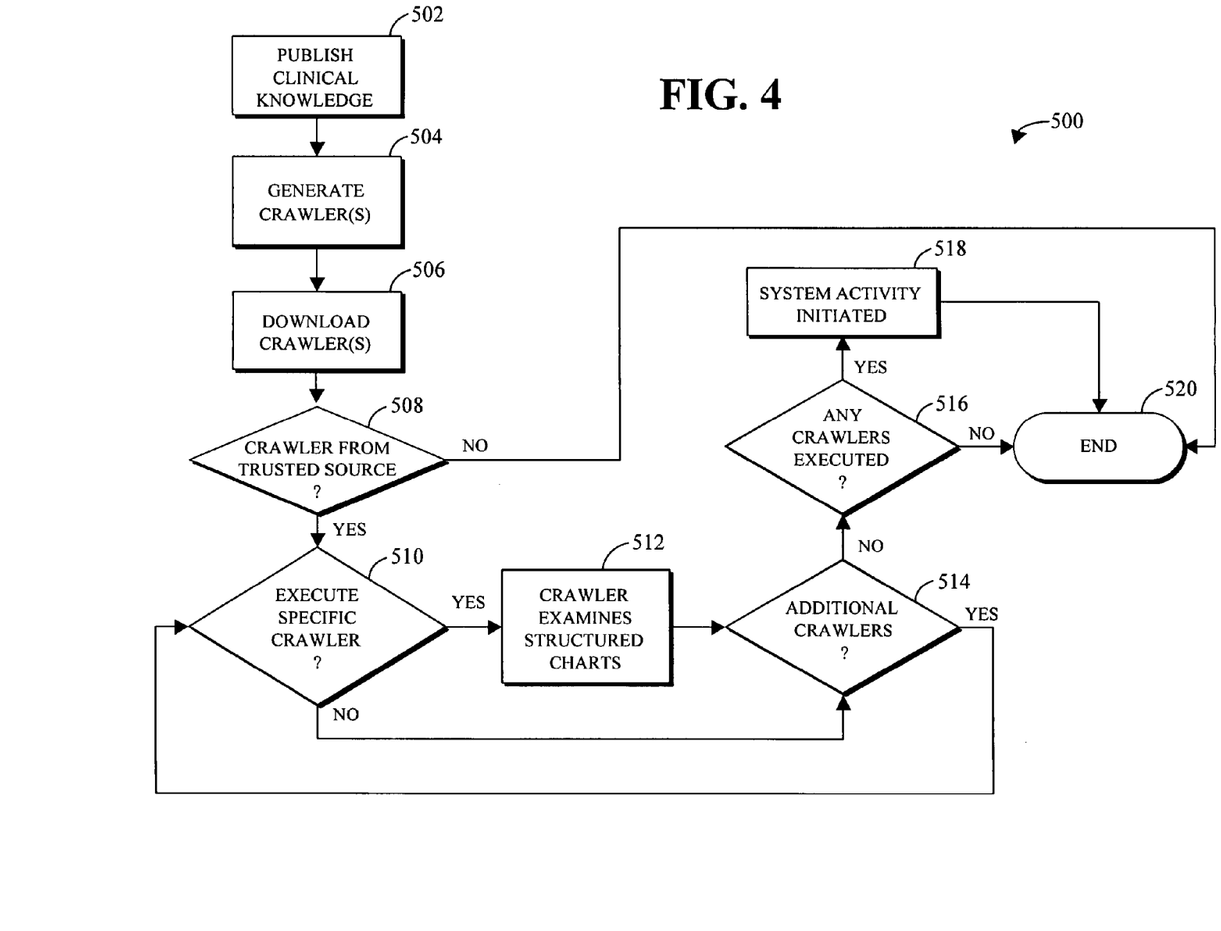
FIG. 4 is a flow diagram of one method for analyzing patient records in which crawlers are distributed to the healthcare entity.

One method 500 for analyzing the electronic patient records 400 of the healthcare entity 300 is depicted in the flow chart of FIG. 4. With respect to this method 500, it should be understood that references to the healthcare entity 300 also include sub-elements of the entity 300 (e.g., individual provider 302 and/or general institution 304).

The method begins with step 502 where specific clinical knowledge generated or otherwise acquired by the Knowledge Service 202 (as an authorized and trusted information source) is published to the Publishing Service 204. Then, in step 504, Publishing Service 204 extracts the necessary information from the communication received from Knowledge Service 202 to generate one or more patient record analyzing crawlers related to the clinical knowledge. The one or more crawlers are "pushed", downloaded or otherwise distributed to the healthcare entity 300 in step 506, preferably without the entity 300 having to request the distribute, such as on a subscription basis.

The healthcare entity 300 then makes a determination in step 508 as to whether the distributed one or more crawlers originate from a trusted source. For instance, the crawlers may include digitally signed code to authenticate that such crawler originated with Publishing Service 204 recognized by the entity. If the crawlers do not originate from the trusted source, then the method moves to endpoint 520. On the other hand, if the crawlers do originate from the trusted source (i.e., Publishing Service 204), then in step 510 another determination is made regarding whether a specific crawler should be executed against the structured charts 402 of a set of electronic patient records 400 of the patient population of the entity 300. This determination may include an evaluation of the relevance of the underlying clinical knowledge with respect to the patient population of the entity 300. Additionally, the determination may be done manually by clinicians or other persons of the healthcare entity 300, or automatically by a computing system of the entity 300 examining the content of the crawler.

If it is determined that the specific crawler should be executed in step 510, then the crawler examines the structured charts 402 of the set of electronic patient records to find matches between the underlying clinical knowledge and information within the structured charts 402, and register such matches, in step 512. The method 500 then proceeds to step 514 to determine if additional crawlers are present. If for some reason it is determined in step 510 that the crawler should not be executed—for example, the underlying clinical knowledge relates to an Alzheimer's standard of care for the elderly, and the healthcare entity 300 only sees pediatric patients—then the method moves directly to step 514 for additional crawler evaluation (if any).

The determination in step 514 determines whether there are any additional crawlers to be executed. If further crawler execution is necessary, then the method returns to step 510 for the specific additional crawler. Conversely, if there are no other crawlers, then in step 516 a determination is made as to whether any crawlers have been executed. If none of the crawlers that were distributed to the healthcare entity 300 have been executed, then the method 500 moves to an endpoint 520. However, if any crawlers have been executed, then in step 518 system activity is initiated based on the registered matches, and optionally, based on the type of the crawler. For example, the system activity may include any of the previously mentioned system activities, such as queuing tasks or automated contacting of patients and/or healthcare providers relevant to the matches among others. The type of crawler may also influence the particular system activity in some cases. One crawler type, as an example, may be authorized to perform automatic contacting of flagged patients and/or their associated providers through pre-established communication means based on contact information stored within the structured charts 402 and/or elsewhere on the system of the healthcare entity 300. The method then concludes at endpoint 520.

Figure 5:
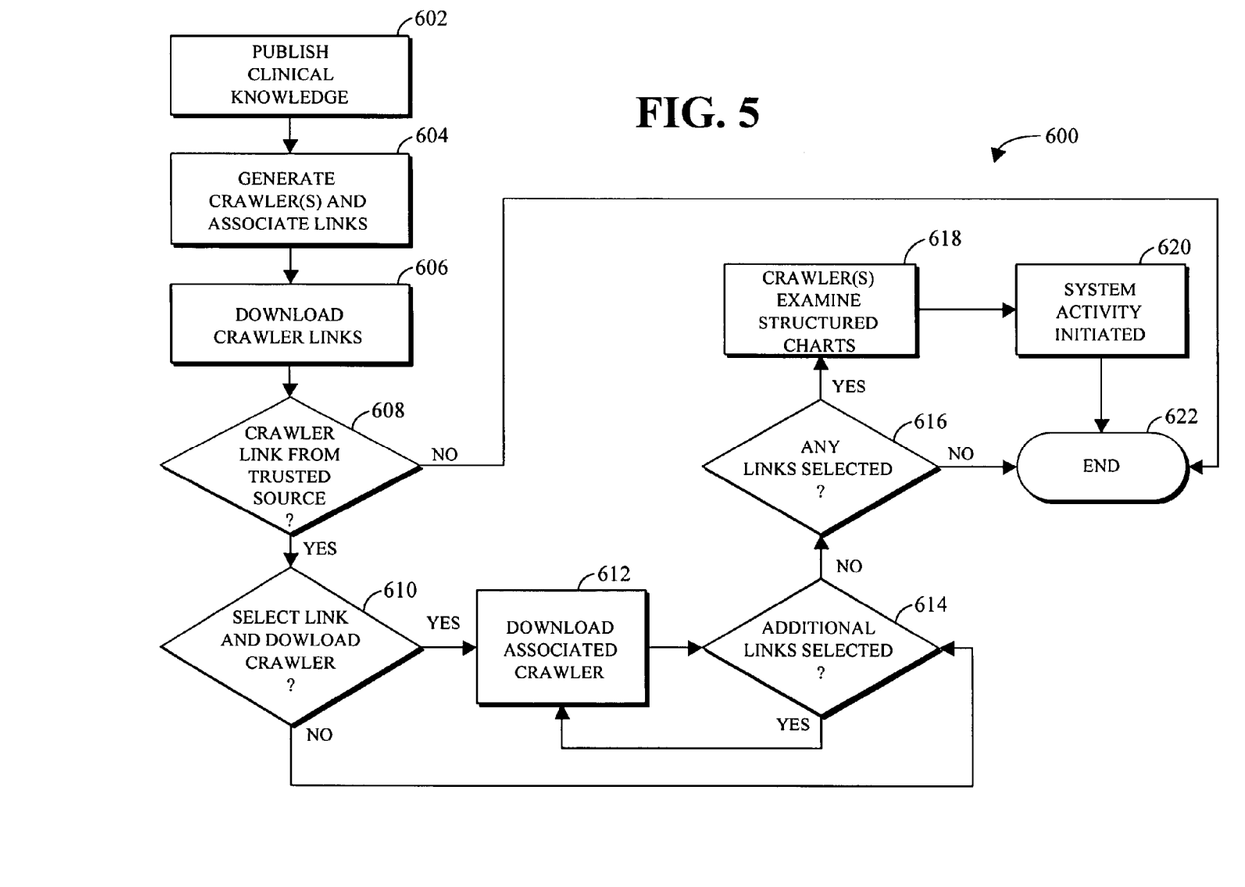
FIG. 5 is a flow diagram of another method for analyzing patient records in which electronic links to crawlers are first distributed to the healthcare entity.

Another method 600 is provided for electronic patient record analysis, and is depicted in the flowchart of FIG. 5. As with the method 500 of FIG. 4, references to the healthcare entity 300 in method 600 also include sub-elements thereof. In step 602, specific clinical knowledge generated or otherwise acquired by the Knowledge Service 202 is published to the Publishing Service 204. Publishing Service 202 receives and uses this clinical knowledge to generate the one or more patient record analyzing crawlers and associated electronic links (e.g., URIs), in step 604. Each electronic link contains information that notifies the healthcare entity 300 generally about the activities or analysis type the crawler will conduct. An associated electronic link for each of the crawlers is then downloaded (or otherwise distributed) to the healthcare entity in step 606.

The healthcare entity 300 then makes a determination in step 608 as to whether the distributed one or more crawler links originate from a trusted source (i.e., Publishing Service 204). If the crawlers do not originate from the trusted source, then the method moves to endpoint 622. On the other hand, if the crawlers do originate from the trusted source, then in step 610, the healthcare entity 300 reviews the electronic link (either manually or automatically through the computing system of the entity 300) to determine whether to select the link and distribute the associated crawler. If the link is selected, then in step 612 distributing of the associated crawler to the healthcare entity 300 occurs. The method 600 moves directly to step 614 if no link is selected.

In step 614, the healthcare entity 300 determines whether to select an additional electronic link, if any, that has been distributed. If an additional link is selected, then the method returns to step 612. If no additional links are selected, then the method 600 moves to step 616 where a determination is made as to whether any links have been selected. If no links have been selected, then the method 600 moves to endpoint 622. Contrastingly, if one or more links have been selected, in step 618, the associated crawlers are executed against the structured charts 402 of the set of electronic patient records 400 of the patient population of the entity 300. Each crawler examines the structured charts 402 of the set of electronic patient records to find matches between the underlying clinical knowledge and information within the structured charts 402, and registers such matches. In step 620, system activity is initiated based on the registered matches, and optionally, based on the type of the crawler. The method then concludes at endpoint 622.

The patient record analyzing abilities provided by the present invention result in improved efficiencies in the delivery of care to a patient population. By employing a preemptive mechanism to examine patient records for certain clinical conditions, healthcare entities 300 can ensure that practicing clinicians are quickly made aware of, and implement, new standard of care guidelines and other clinical knowledge that affect their patients. Because a given healthcare entity 300 has the ability to review crawlers related to pieces of clinical knowledge, the entity 300 retains some control over the implementation of the analysis. The present invention therefore facilitates achieving a global/local balance of control in that more centralized trusted organizations are responsible for generating and regulating the flow of clinical knowledge, but the individual healthcare entities 300 have some decision making power as to whether and how that clinical knowledge will be used for analyzing patient records of the entity 300. Preferably, the component modules 200 support an open architecture so that the methods of the present invention may be employed on a large, distributed scale throughout one or more given healthcare entities 300.

Furthermore, since certain changes may be made in the above invention without departing from the scope hereof, it is intended that all matter contained in the above description or shown in the accompanying drawing be interpreted as illustrative and not in a limiting sense.

Having thus described the invention, what is claimed is:

1. Non-transitory computer storage media storing computer-useable instructions that, when used storing computer-useable instructions that, when used by one or more computing devices, cause the one or more computing devices to perform a method for analyzing a set of records of a healthcare entity's patient population with respect to a piece of clinical knowledge embodied in executable code, comprising:

receiving a public health informational publication from a third-party publication source recognized by the healthcare entity as an authority for medical or healthcare-related clinical knowledge;

analyzing the public health informational publication for a relevant piece of clinical information comprising an alert about a specific public health situation;

extracting the relevant piece of clinical information from the public health informational publication;

transforming the relevant piece of clinical information into executable code;

distributing a uniform resource indicator (URI) to at least a portion of the executable code to the healthcare entity, wherein selection of the URI by the healthcare entity initiates execution of the at least the portion of the executable code against a set of structured electronic patient records of the patient population of the healthcare entity to register matches of the relevant piece of clinical information with data contained in the set of structured electronic patient records, wherein the matches correspond to a portion of the patient population; and queuing and ranking patients within the portion of the patient population according to a degree of matching between the relevant piece of clinical information and the each patient's data contained in the set of structured electronic patient records.

2. The media of claim 1, wherein the set of structured electronic patient records pertains to individual patients within the patient population.

3. The media of claim 1, wherein the executable code includes an executable macro.

4. The media of claim 1, wherein the alert about the specific public health situation relates to at least one of a drug-drug, a drug-allergy, or a food-allergy interaction.

5. The media of claim 1, wherein the healthcare entity is at least one of a healthcare institution or an individual healthcare provider.

6. The media of claim 1, wherein prior to selection of the URI to the at least the portion of the executable code, the healthcare entity verifies that the URI originates from a trusted source.

7. The media of claim 1, wherein the data contained in the set of structured electronic patient records comprises one or more of information entered by a clinician, patient-identifying information, insurance information, financial information, patient health status, physiological conditions, medications, immunizations, food allergies, drug allergies, diagnoses by clinicians, and care documentation.

8. The media of claim 7, wherein physiological conditions comprise one or more of blood pressure, oxygen saturation in blood, or patient vital signs, and wherein care documentation comprises one or more of a listing of current clinicians providing care to the patient or a listing of past clinicians that have provided care to the patient.

9. Non-transitory computer storage media storing computer-useable instructions that, when used storing computer-useable instructions that, when used by one or more computing devices, cause the one or more computing devices to perform a method for analyzing a set of records of a healthcare entity's patient population with respect to a piece of clinical knowledge embodied in executable code, comprising:

receiving a public health informational publication from a third-party publication source recognized by the healthcare entity as an authority for medical or healthcare-related clinical knowledge;

analyzing the public health information publication for a relevant piece of clinical information comprising an alert about a specific public health situation;

extracting the relevant piece of clinical information from the public health informational publication;

transforming the relevant piece of clinical information into executable code;

distributing a uniform resource indicator (URI) to at least a portion of the executable code to the healthcare entity, wherein selection of the URI by the healthcare entity initiates execution of the at least the portion of the executable code against a set of structured electronic patient records of the patient population of the healthcare entity to register matches of the relevant piece of clinical information with data contained in the set of structured electronic patient records, wherein the matches correspond to a portion of the patient population;

based on the registered matches, automatically contacting patients within the portion of the patient population to apprise them of the alert about the specific public health situation; and based on the registered matches, automatically notifying one or more clinicians associated with the portion of the patient population of the alert about the specific public health situation.

10. The media of claim 9, further comprising based on the registered matches generating reports about the matching results, and editing standard of care guidelines for clinicians.

* * * * *